United States Patent
Buonanato

(10) Patent No.: US 6,861,554 B2
(45) Date of Patent: Mar. 1, 2005

(54) CREATINE SALT HAVING ENHANCED NUTRITIONAL AND THERAPEUTIC EFFICACY AND COMPOSITIONS CONTAINING SAME

(75) Inventor: Antonietta Buononato, Rome (IT)

(73) Assignee: Biosalts s.r.l., Rome (IT)

(*) Notice: Subject to any disclaimer, the term of this patent is extended or adjusted under 35 U.S.C. 154(b) by 82 days.

(21) Appl. No.: 10/258,878

(22) PCT Filed: Mar. 19, 2002

(86) PCT No.: PCT/IT02/00170
§ 371 (c)(1),
(2), (4) Date: Oct. 30, 2002

(87) PCT Pub. No.: WO02/076931
PCT Pub. Date: Oct. 3, 2002

(65) Prior Publication Data
US 2003/0180276 A1 Sep. 25, 2003

(30) Foreign Application Priority Data
Mar. 23, 2001 (IT) .................... RM2001A0155

(51) Int. Cl.⁷ .................... C07C 229/00; C07C 409/00
(52) U.S. Cl. .................... 562/561; 562/500; 568/30; 424/439; 424/44; 424/145; 424/464
(58) Field of Search .................... 562/561, 560; 568/30; 424/400, 439, 441, 451, 464, 489; 514/948, 951, 960, 962

(56) References Cited

U.S. PATENT DOCUMENTS 5,817,329 A * 10/1998 Gardiner .................... 424/439

FOREIGN PATENT DOCUMENTS

| WO | 98 43617 A | * 10/1998 |
| WO | 01 17948 A | * 3/2001 |

* cited by examiner

Primary Examiner—Thurman K. Page
Assistant Examiner—Sharmila S. Gollamudi
(74) Attorney, Agent, or Firm—Nixon & Vanderhye P.C.

(57) ABSTRACT

A novel salt, creatine taurinate, and the compositions containing same (health foods, dietary supplements or drugs) are disclosed.

7 Claims, No Drawings

CREATINE SALT HAVING ENHANCED NUTRITIONAL AND THERAPEUTIC EFFICACY AND COMPOSITIONS CONTAINING SAME

This application is the US national phase of international application PCT/IT02/00170 filed 19 Mar. 2002, which designated the US.

The present invention relates to a novel stable and non-hygroscopic creatine salt having enhanced nutritional and/or therapeutic efficacy and also relates to the compositions which can be used as energizing dietary supplements, nutraceuticals, health foods and drugs containing said salt as active ingredient.

More particularly, such novel compound is the salt of creatine with taurine which hereinbelow will be referred to as creatine taurinate, During last years, the use of dietary supplements, nutraceuticals and health foods containing substances of natural origin as active ingredients has become more and more widespread, arousing the interest of ever wider consumers classes.

Creatine is but one of the natural products which, thanks to its physiologic activity, has brought about a major interest both in the scientific community and the consumers.

Creatine is an organic, nitrogen compound present in considerable amounts in the skeletal muscle tissue of vertebrates wherein about 2/3 thereof occurs as creatine phosphate.

Creatine is biosynthesized mainly in the liver and kidneys from three amino acids: glycine which provides the carbon skeleton, arginine which releases the amidino group and methionine which releases the methyl group. Creatine is excreted with urine as creatinine. Creatine can be taken with the diet since it is principally present in meat. However, in order to take 10 grams/day of creatine, 2.5 kg of meat should be eaten. The exogenous supply and endogenous biosynthesis must compensate for the daily turn-over of creatine to creatinine which in a 70-kg male subject can be estimated at about two grams.

The physiologic role of creatine is extremely important: principally in the skeletal muscle, but in the brain, liver and kidneys as well, creatine—by reversibly taking up ATP's phosphate groups—plays the role of reservoir of the energy-rich phosphate radicals. This reaction is critically important since ATP can not be stored in tissues in excess of a very limited threshold. It is creatine phosphate whose content in tissues is five times as much that of ATP, which provides for phosphate groups supply. Following a moderately wearying physical exertion, the creatine phosphate present in the skeletal muscle decreases in a far relevant amount than ATP does, thus showing that creatine phosphate rephosphorilates ADP as ATP becomes dephospharilated.

When the rate of ATP's metabolic production exceeds ATP's utilization, this results in creatine phosphate formation. Creatine phosphate is, therefore, a reservoir of immediately available energy, suitable for counterbalancing energy demands exceeding ATP's synthesis rate in metabolic phosphorylation processes.

Creatine is mainly taken by athletes and sportsman insofar as it increases the skeletal musculature if its intake is accompanied by lasting physical exertion. Creatine intake results in a lowering of fat while it enhances skeletal muscle. Recent researches have shown that the combined intake of creatine and carbohydrates enhances creatine effects owing to insuline production that is stimulated by simple sugars which likely play a role in creatine exportation to muscle cells.

Taurine (2-aminoethanesulphonic acid) is one of the most plentiful aminoacids in the body: it is found in the central nervous system, in skeletal muscles and is particularly concentrated in the brain and heart.

It has long since been known to be an essential nutrient during mammalian growth and development and is, infact, present in mother's milk and is especially important for the development of the cerebellum and retina.

Taurine also performs a very important metabolic function: in the bile, the bile acids bind with taurine to form glycocholic and taurocholic acids, respectively.

The salts of bile acids possess the important property of lowering the surface tension of solutions. For this reason, they are excellent emulsifiers and perform an important function in the uptake and digestion of lipids in the bowel.

A deficit in taurine is linked to retina degeneration. Diabetics generally exhibit low levels of taurine in the blood and platelets. Taurine administration to insulino-dependent diabetics has been shown to decrease platelet aggregation and prevent retinopathy counteracting haematic aggregation in retina's vasa.

Furthermore, taurine mimics and supports insuline action, a property found in 1942 and recently "rediscovered" [Amer. Clin. Intr., 71: 54–58 (2000)] and improves creatine uptake.

It has now been found that the novel creatine taurinate salt having formula

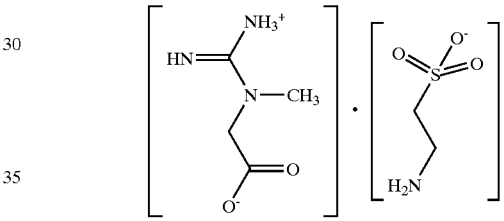

is a stable, non hygroscopic compound endowed with synergistic activity with respect to creatine and taurine. In the following table, the percentages of increase in the glucose uptake by the muscle cells with respect to insulin are shown.

TABLE 1

| Substance | Grams | Glucose uptake |
| --- | --- | --- |
| Taurine | 2.5 | 15–18% |
| Creatine monohydrate | 2.5 | 1–2% |
| Taurine + Creatine | 5.0 | 18–20% |
| Creatine taurinate | 5.0 | 25–28% |

In the following example the preparation and physico-chemical properties of the compound of the invention are shown.

EXAMPLE

Creatine Taurinate (BS 227)

14.9 g (0.1 moles) of creatine monohydrate and 12.5 g (0.1 moles) of taurine were dissolved in the minimum amount of water. Isobutanol was added to the resulting solution and the mixture thus obtained concentrated under vacuum by means of azeotropic distillation. A residue was obtained which was taken up with acetone, filtered off and dried under vacuum in a thermostatic oven at 40° C. overnight.

25,3 of creatine taurinate as a crystalline white solid were obtained, yeild: 93,7%. The salt thus obtained can be crystallized with methanol resulting in macrocrystals having the same physico-chemical properties as the raw material.

M.P. 147–149° C.

K.F. 1,2% pH 6,5 (c=1%)

| Elementary Analysis: | C% | H% | N% | S% |
|---|---|---|---|---|
| Calculated: | 28.15 | 6.25 | 21.8 | 12.5 |
| Found: | 28.01 | 6.11 | 21.82 | 12.39 |

NMR: $D_2O$=3,9 (2H,S,$\underline{CH_2}$—COOH); 3,4–3,3 (2H, t, NH—$\underline{CH_2}$); 3,2–3,1 (2H, t, $\underline{CH_2}$—$SO_3$); 3(3H, s, N—$\underline{CH_3}$)

HPLC: column: Hypersil APS-2 (5 µm) 200 ×4,4; temperature: 30° C.

Mobile Phase: $CH_3CN/H_2O$+0,05 M—$KH_2PO_4$/$CH_3CN$ (65–35 v/v); pH 4,7 with $H_3PO_4$ Flow rate: 0,7 ml/min: Taurine: Rt=5,3; Creatine: Rt=7,3

The compositions of the invention comprising creatine taurinate as active ingredient may also comprise, in addition to the usual pharmacologically acceptable excipients whose selection is within the reach of the average skilled expert in pharmacy, further active principles, aminoacids, antioxidants, mineral substances, vitamins and coenzymes.

Preferred, although non-limiting, examples of these further ingredients are α-lipoic acid (whose antioxidant and scavenging activity towards toxic metals have long since been known), L-carnitine, acetyl L-carnitine, coenzyme $Q_{10}$ and the bioavailable forms of mineral substances such as selenium, magnesium and zinc, e.g. selenomethionine.

The compositions can be administered in the form of tablets, chewable tablets, capsules, sachets, granulates, powders, syrups and drops. The compositions in unit dosage form comprise from about 50 to 500 mg, preferably from about 150 to 250 mg, of creatine taurinate.

What is claimed is:

1. Creatine taurinate of formula:

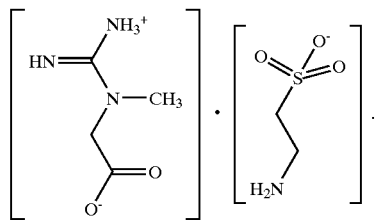

2. A composition comprising creatine taurinate as active ingredient and a pharmacologically acceptable excipient.

3. The composition of claim 2, comprising at least one further ingredient selected from active principles, aminoacids, antioxidants, mineral substances, vitamins and coenzymes.

4. The composition of claim 3, wherein the further ingredient is selected from the group comprising L-carnitine, acetyl L-carnitine, α-lipoic acid, coenzyme Q10 and bioavailable compounds of selenium, magnesium and zinc.

5. The composition of claim 2 in the form of tablets, chewable tablets, capsules, sachets, granulates, powders, syrups and drops.

6. The composition of claim 2 in unit dosage form, comprising 50–500 mg, preferably 150–250 mg, of creatine taurinate.

7. The composition of claim 2 for human consumption as dietary supplement, nutraceutical, health food or drug.

* * * * *